United States Patent [19]
Ishiguro et al.

[11] Patent Number: 4,985,575
[45] Date of Patent: Jan. 15, 1991

[54] PROCESS FOR PREPARING OPTICALLY ACTIVE TETRAHYDRO-2-FUROIC ACID

[75] Inventors: Masaji Ishiguro; Hiromitsu Iwata; Takashi Nakatsuka, all of Osaka; Kiyoharu Nakayama, Tokyo; Osamu Miyahara, Toyama; Kenichi Noguchi, Toyama, all of Japan

[73] Assignees: Suntory Limited, Osaka; Nippon Soda Co., Ltd., Tokyo, both of Japan

[21] Appl. No.: 475,801

[22] Filed: Feb. 6, 1990

[30] Foreign Application Priority Data

Feb. 7, 1989 [JP] Japan .................................. 1-28511

[51] Int. Cl.$^5$ ........................................... C07D 307/24
[52] U.S. Cl. .................................................. 549/484
[58] Field of Search ........................................ 549/484

[56] References Cited

U.S. PATENT DOCUMENTS 4,950,772  8/1990  Nohira et al. .................... 549/484

FOREIGN PATENT DOCUMENTS 1216983  8/1989  Japan .

OTHER PUBLICATIONS

Nohira et al., Chemical Abstracts, vol. 110 (1989) 94589p.

Primary Examiner—Richard L. Raymond
Attorney, Agent, or Firm—Oblon, Spivak, McClelland, Maier & Neustadt

[57] ABSTRACT

A process for preparing an optically active tetrahydro-2-furoic acid is disclosed. The process comprises (i) reacting (±)-tetrahydro-2-furoic acid with an optically active amine resolver of the following formula (I):

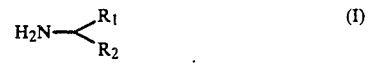

wherein $R_1$ is a lower alkyl group and $R_2$ represents an alkyl group or ar aryl group, provided that $R_1$ and $R_2$ are different from each other, thus producing an optically active diastereomer salt, and (ii) decomposing the diastereomer salt. According to the process, a high purity, optically active tetrahydro-2-furoic acid can be prepared at a high yield using an amine resolver. The amine resolver can be recovered at a high yield and high purity.

5 Claims, No Drawings

PROCESS FOR PREPARING OPTICALLY ACTIVE TETRAHYDRO-2-FUROIC ACID

BACKGROUND OF THE INVENTION

1. Field of the Invention

The present invention relates to a process for preparing an optically active tetrahydro-2-furoic acid, and, more particularly, to a process for preparing an optically active tetrahydro-2-furoic acid which comprises reacting ($\pm$)-tetrahydro-2-furoic acid with a specific type of optically active amine resolver to produce an optically active diastereomer salt, followed by decomposition of the diastereomer salt.

2. Description of the Background Art:

In recent years, requirement for the use of optically active compounds for in the fields of pharmaceuticals, agrichemicals, foods, and the like is increasing. Conventionally, preparing optically active compounds involves difficulties in terms of production cost and manufacturing processes. Because of this, DL compounds have been used in many cases instead of optically active compounds. This, however, may bring about problems in case where one of the optical isomers is inactive or exhibits adverse side effects as in the case of thalidomide. For this reason, production of optically active pharmaceuticals is an important subject.

An optically active tetrahydro-2-furoic acid which is the subject of the present invention is expected to be used as an important pharmaceutical raw material as reported by P. C. Belanger et al. [*Can. J. Chem.* 61, 1383 (1983)] and by Japanese Patent Laid-open No. 207387/1986. One of the conventionally known processes for resolving optically active tetrahydro-2-furoic acids is that proposed by P. C. Belanger et al. This process involves the use of brucine dihydrate, which is an extremely expensive and highly toxic substance. In addition, its recovery rate is very low. Because of these reasons, great deal of improvement has to be done for the process to be industrially applied.

In this situation, for the purpose of developing a more practical process the present inventors have undertaken extensive studies, including investigations on the resolving agents, solvents, reaction conditions, methods of resolver recovery, and the like. As a result, the present inventors were successful in preparing the target optically active tetrahydro-2-furoic acid by reacting ($\pm$)-tetrahydro-2-furoic acid with an optically active amine resolver having the formula (I) hereinafter given to produce an optically active diastereomer salt and by decomposing the diastereomer salt. The inventors have further developed a process in which the resolver could be recovered at a high yield and a high purity and a higher reaction concentration could be used. A mass-production of the optically active tetrahydro-2-furoic acid was also realized by the use of the process.

SUMMARY OF THE INVENTION

Accordingly, an object of the present invention is to provide a process for preparing an optically active tetrahydro-2-furoic acid comprising:

reacting ($\pm$)-tetrahydro-2-furoic acid with an optically active amine resolver of the following formula (I):

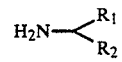

wherein $R_1$ is a lower alkyl group and $R_2$ represents an alkyl group or an aryl group, provided that $R_1$ and $R_2$ are different from each other, thus producing an optically active diastereomer salt, and decomposing the diastereomer salt.

Other objects, features, and advantages of this invention will appear more fully from the following description.

DETAILED DESCRIPTION OF THE INVENTION AND PREFERRED EMBODIMENTS

In the process of the present invention ($\pm$)-tetrahydro-2-furoic acid is first reacted with an optically active amine resolver of the formula (I) in a solvent to produce a diastereomer salt. The ratio of ($\pm$)-tetrahydro-2-furoic acid to the optically active amine resolver used in the reaction is in the range of 2:1 to 1:1.5, with the particularly preferable ratio being 1.5:1 to 1:1.

In the formula (I) which represents the optically active amine resolver used in the present invention, the group $R_1$ is an alkyl group having 1–5, preferably 1–3, carbon atoms. The group $R_2$ may be an alkyl group having carbon atoms of more than 6, preferably of 6–10, and includes a cyclo alkyl group such as cyclohexyl or a branched alkyl group, or may be an aryl group such as phenyl group or naphthyl group. The aryl group may have an substituent such as an alkyl group on its ring.

The optically active amines used in the present invention include, but not limited to, 1-cyclohexylethylamine, 1-phenylethylamine, 1-(1-naphthyl)ethylamine, 1-p-tolylethylamine, and the like.

Given as reaction solvents are esters such as methyl acetate, ethyl acetate, and the like; alcohols, such as methanol, ethanol, and the like; ketones such as acetone and the like; nitriles such as acetonitrile and the like; halogenated hydrocarbons such as methylene chloride, chloroform, monochlorobenzene, and the like; ethers such as tetrahydrofuran, dioxane, and the like; and aromatic hydrocarbons such as toluene, benzene, and the like. These solvents may be used independently or as a mixture of two or more. The reaction temperature can be from room temperature to the boiling point of the solvent used. A preferable method is to heat the reaction mixture to 40–70° C. to make it into a homogeneous solution, and then to gradually cool it to a temperature at which the diastereomer salt precipitates.

The precipitated diastereomer salt is separated by filtration, and subjected to recrystallization using the same solvent which is used when producing the diastereomer salt, thus obtaining the target high purity diastereomer salt.

For decomposing the diastereomer salt, an alkaline solution such as an aqueous solution of sodium hydroxide or potassium hydroxide is added to it to make the pH to 11–14. After separating the organic layer, the water layer is washed with an organic solvent to eliminate impurities, adjusted to pH 1–2 by a mineral acid such as a dilute hydrochloric acid or sulfuric acid, and extracted with an organic solvent to obtain the target optically active tetrahydro-2-furoic acid. The product thus produced has a sufficient purity and can be used for the next reaction in most cases. If required, the product can be further purified by a suitable means such as distillation or the like.

There are no specific restrictions as to the solvent which is used in the extraction so long as the same is not miscible with water. The use of the same solvent as used for the production of diastereomer salt is desirable for a more integrated design of the process and for effective recovery of the solvent.

The resolver used in the reaction can be recovered from the mother liquor obtained from the diastereomer salt reaction mixture. After the addition of water and extraction of the diastereomer salt, an organic solvent and alkaline solution is added to make the pH to 11–14. Water is separated off and the organic layer obtained from the diastereomer salt decomposition reaction is added to the organic layer, followed by washing with water, drying, and evaporating the solvent. The residue thus obtained is purified by distillation to recover the resolver at a high purity and a high yield.

Other features of the invention will become apparent in the course of the following description of the exemplary embodiments which are given for illustration of the invention and are not intended to be limiting thereof.

EXAMPLES

In the Examples, the optical purity (enantiometric excess: ee) of diastereomer salts are determined by the following method.

Ether was added to the diastereomer salt crystals prepared in Examples. Several drops of concentrated hydrochloric acid were then added to the mixture while vigorously stirring, followed by an addition of an excess amount of diazomethane and stirring for about 10 minutes. The mixture was dried over anhydrous magnesium sulfate. Insoluble components were separated by filtration and the filtrate was subjected to HPLC analysis using a SUMIPAX OA 2000 column (4.6 mm I.D. ×250 mm, 5 μm). A deaerated mixed solvent of haxane-ethylene dichloride (750:150) was used as a mobile phase at a flow rate of 1.2 ml/min. Detection was made by UV light (220 nm). When the standard sample was analyzed under these conditions R-form eluted at 7.64 minute and S-form at 8.41 minute.

Example 1

A mixture of (S)-(−)-1-phenylethylamine (12.12 g), (±)-Tetrahydro-2-furoic acid (11.61 g), and tetrahydrofuran (100 ml) was heated under refluxing. After complete dissolution, the mixture was gradually cooled and allowed to stand still at room temperature for two hours. Precipitated crystals were collected by filtration to obtain primary crystals (10.74 g). The primary crystals were twice recrystallized from tetrahydrofuran (134 ml for each recrystallization) to produce 5.97 g diastereomer salt as colorless needle-like crystals. The optical purity of this compound was found to be 98.0% e.e. by HPLC analysis. (R)-(+)-Tetrahydro-2-furoic acid was obtained by decomposing the salt.

Examples 2–11

Reactions were carried out in the same manner as in Example 1, except for using the conditions, the solvents, and the solvent amount listed in Table 1. The products had optical purities shown in Table 1.

TABLE 1

| Example | Solvent Kind | Amount (ml) | Yield (%) | e.e. (%) |
| --- | --- | --- | --- | --- |
| 2 | Methylene chloride | 100 | 44 | 47 |
| 3 | Tetrahydrofuran | 80 | 46 | 58 |
| 4 | Acetone | 80 | 41 | 52 |
| 5 | Toluene | 300 | 52 | 61 |
| 6 | Monochlorobenzene | 100 | 53 | 54 |
| 7 | Ethyl acetate | 120 | 50 | 65 |
|   | Chloroform | 80 |   |   |
| 8 | Ethyl acetate | 120 | 43 | 62 |
|   | Methylene chloride | 60 |   |   |
| 9 | Toluene | 120 | 46 | 64 |
|   | Methylene chloride | 30 |   |   |
| 10 | Ethanol | 20 | 34 | 67 |
|   | Chloroform | 70 |   |   |
| 11 | iso-Propanol | 20 | 43 | 68 |
|   | Chloroform | 70 |   |   |

(R)-(+)-Tetrahydro-2-furoic acid was obtained by decomposing the salts prepared in the above examples.

Examples 12–14

(S)-(−)-1-(1-Naphthyl)ethylamine (59 mg) and (±)-tetrahydro-2-furoic acid (40 mg) were treated with solvents shown in Table 2 in the same manner as in Example 1. Yields and optical purities of the primary crystals are shown in Table 2.

TABLE 2

| Example | Solvent | Yield (%) | e.e. (%) |
| --- | --- | --- | --- |
| 12 | Tetrahydrofuran | 44 | 55 |
| 13 | Dioxane | 55 | 58 |
| 14 | iso-Propanol | 51 | 36 |

(R)-(+)-Tetrahydro-2-furoic acid was obtained by decomposing the salts prepared in the above examples.

Examples 15–16

(R)-(+)-1-(1-Naphthyl)ethylamine (236 mg) and (±)-tetrahydro-2-furoic acid (160 mg) were treated with solvents shown in Table 3 in the same manner as in Example 1. Yields and optical purities of the secondary crystals are shown in Table 3.

TABLE 3

| Example | Solvent | Yield (%) | e.e. (%) |
| --- | --- | --- | --- |
| 15 | Tetrahydrofuran | 52 | 83 |
| 16 | Acetone | 46 | 85 |

(S)-(−)-Tetrahydro-2-furoic acid was obtained by decomposing the salts prepared in the above examples.

Example 17

(S)-(−)-1-(p-Tolyl)ethylamine (47 mg) and (±)-tetrahydro-2-furoic acid (40 mg) were treated with the solvent shown in Table 4 in the same manner as in Example 1. The yield and optical purity of the primary crystals are shown in Table 4.

TABLE 4

| Example | Solvent | Yield (%) | e.e. (%) |
| --- | --- | --- | --- |
| 17 | Acetone | 33 | 68 |

(R)-(+)-Tetrahydro-2-furoic acid was obtained by decomposing the salt.

Example 18

Methylene chloride (550 ml) and ethyl acetate (1,100 ml) were added to (±)-tetrahydro-2-furoic acid (116.1 g). (S)-(−)-1-phenylethylamine (121.2 g) was added dropwise, and the mixture was heated under refluxing for 15 minutes. After gradually cooling the resulting reaction mixture to 20° C. over 2 hours, precipitated crystals were separated by filtration. The filtrate was used for recovering the amine. The crystals were dried to obtain 111.5 g of the primary crystals. The optical purity of the crystals was measured by HPLC analysis (yield: 47%, optical purity: 59% e.e.).

Methylene chloride (550 ml) and ethyl acetate (1,100 ml) were added to the 111.5 g of primary crystals and the mixture was heated under refluxing for 15 minutes. After gradually cooling the resulting reaction mixture to 20° C. over 2 hours, precipitated crystals were separated by filtration. The filtrate was used for recovering the amine. The crystals were dried to obtain 80.7 g of the secondary crystals. The optical purity of the crystals was measured by HPLC analysis (yield: 34%, optical purity: 91% e.e.).

The same procedure as above was repeated on 80.7 g of the secondary crystals to produce 75.9 g of ternary crystals (yield: 32%, optical purity: 99% e.e.).

Water (20 g) and methylene chloride (160 ml) were added to the 75.9 g of ternary crystals. To the mixture were added 45.9 g of 28% aqueous solution of sodium hydroxide to make the pH to 13, thus decomposing the diastreomer salt. The water layer was separated, and washed with methylene chloride. Methylene chloride layers were collected for the recover of the amine. After an addition of methylene chloride (160 ml), the washed water layer was adjusted to pH 1 with concentrated hydrochloric acid (40.9 g) and separated. The water layer was further extracted four times with methylene chloride (160 ml for each extraction). Methylene chloride layers were combined, concentrated, and distilled under reduced pressure (108° C., 10 mmHg) to produce 34.8 g of optically active (R)-(+)-tetrahydro-2-furoic acid (yield: 30%, optical purity: 99% e.e.).

The primary, secondary, and ternary crystals were mixed and extracted twice with 100 ml of water. The water layer was combined and to this was added 200 ml of methylene chloride. The mixture was adjusted to pH 13 with 28% aqueous solution of sodium hydroxide (99.8 g) and the water layer and methylene chloride layer was separated. The water layer was again extracted with 200 ml of methylene chloride. The methylene chloride layers were combined, and to this was added the methylene chloride layer obtained when decomposing the diastereomer salt. The mixture was concentrated, and distilled under reduced pressure (65° C., 10 mmHg) to produce 112.7 g of (S)-(−)-phenylethylamine (recovery rate: 93%).

The specific rotation of the recovered product was measured and found to be $[\alpha]_D = -38.4°$ C. (neat), which was almost the same as the value $[\alpha]_D = -38.5°$ C. (neat) for the fresh (S)-(−)-phenylethylamine used in the experiment. The recovered (S]-(−)-phenylethylamine was repeatedly used for the experiment and found to give the same results as the fresh one.

Example 19

Monochlorobenzene (1,200 l) was added to (±)-tetrahydro-2-furoic acid (116.1 kg). To this mixture (S)-(−)-1-phenylethylamine (121.2 kg) was added dropwise over 2 hours. The mixture was heated to dissolution and reacted at 65° C. for 30 minutes. After gradually cooling to the resulting reaction mixture 20° C. over 6 hours, precipitated crystals were separated by centrifugation to obtain 144.4 kg of wet primary crystals. A portion of the crystals was dried to determine the yield and to measure optical purity by HPLC analysis (yield: 41%, optical purity: 74% e.e.).

Monochlorobenzene (1,200 l) was added to the 144.4 kg of the wet primary crystals and heated to dissolution. After reaction at 74° C. for 30 minutes, the solution was gradually cooled to 20° C. over 6 hours. The precipitated crystals were separated by centrifugation to obtain 116.4 kg of wet secondary crystals. A portion of the crystals was dried to determine the yield, and to measure optical purity by HPLC analysis (yield: 33%, optical purity: 92% e.e.).

The same procedure as above was repeated on the 116.4 kg of wet secondary crystals to produce 83.4 kg of wet ternary crystals. 73.5 kg of dry ternary crystals were obtained by drying the wet crystals (yield: 31%, optical purity: 98% e.e.).

Decomposition of diastereomer salt was carried out using the 73.5 g of dry ternary crystals in the same manner as in Example 18 to produce 33.7 kg of optically active (R)-(+)-tetrahydro-2-furoic acid (yield: 29%, optical purity: 98% e.e.).

The amine was recovered in the same manner as in Example 18 to obtain 116.4 kg of (S)-(−)-phenylethylamine (recovery rate: 96%) having a specific rotation of $[\alpha]_D = -38.4°$ C. (neat).

As described above, according to the process of the present invention a high purity, optically active tetrahydro-2-furoic acid can be prepared at a high yield using an amine resolver which is less toxic and more readily available than brucine used in conventional processes. In addition the amine resolver can be recovered at a high yield and high purity.

Obviously, numerous modifications and variations of the present invention are possible in light of the above teachings. It is therefore to be understood that within the scope of the appended claims, the invention may be practiced otherwise than as specifically described herein.

What is claimed is;

1. A process for preparing an optically active tetrahydro-2-furoic acid comprising:
   reacting (±)-tetrahydro-2-furoic acid with an optically active amine resolver selected from the group consisting of 1-cyclohexylethylamine, 1-phenylethylamine, 1-(1naphthyl)ethylamine and 1-p-tolylethylamine,

thus, producing an optically active diastereomer salt, and
   decomposing the diastereomer salt.

2. The process of claim 1 wherein the amine resolver is 1-cyclohexylethylamine.

3. The process of claim 1 wherein the amine resolver is 1-phenylethylamine.

4. The process of claim 1 wherein the amine resolver is 1-(1-naphthyl)ethylamine.

5. The process of claim 1 wherein the amine resolver is 1-p-tolylethylamine.

* * * * *

UNITED STATES PATENT AND TRADEMARK OFFICE
CERTIFICATE OF CORRECTION

PATENT NO. : 4,985,575
DATED : January 15, 1991
INVENTOR(S) : Masaji Ishiguro, et al It is certified that error appears in the above-indentified patent and that said Letters Patent is hereby corrected as shown below:

Column 6, line 51, Claim 1, "1-(1napthyl)" should read --1-(1-naphthyl)-;
   line 53-55, delete formula (I) in its entirety.

Signed and Sealed this

Twelfth Day of April, 1994

*Attest:*

BRUCE LEHMAN

*Attesting Officer*

Commissioner of Patents and Trademarks